(12) United States Patent
Siccardi et al.

(10) Patent No.: US 11,357,519 B2
(45) Date of Patent: Jun. 14, 2022

(54) CUTTING GUIDE FOR PERIACETABULAR OSTEOTOMY AND KIT FOR PERIACETABULAR OSTEOTOMY

(71) Applicant: MEDACTA INTERNATIONAL SA, Castel San Pietro (CH)

(72) Inventors: Francesco Siccardi, Castel San Pietro (CH); Sascha Berberich, Castel San Pietro (CH); Matteo Ponzoni, Castel San Pietro (CH); Matteo Ferrari, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 38 days.

(21) Appl. No.: 16/956,253

(22) PCT Filed: Dec. 17, 2018

(86) PCT No.: PCT/IB2018/060161
§ 371 (c)(1),
(2) Date: Jun. 19, 2020

(87) PCT Pub. No.: WO2019/123193
PCT Pub. Date: Jun. 27, 2019

(65) Prior Publication Data
US 2021/0077130 A1 Mar. 18, 2021

(30) Foreign Application Priority Data
Dec. 22, 2017 (IT) .................. 102017000148753

(51) Int. Cl.
*A61B 17/17* (2006.01)
*A61B 17/15* (2006.01)
*A61B 17/56* (2006.01)

(52) U.S. Cl.
CPC ........ *A61B 17/1746* (2013.01); *A61B 17/151* (2013.01); *A61B 17/152* (2013.01);
(Continued)

(58) Field of Classification Search
CPC .............. A61B 17/1746; A61B 17/151; A61B 17/8866; A61B 17/86; A61B 17/15;
(Continued)

(56) References Cited

U.S. PATENT DOCUMENTS 5,112,337 A * 5/1992 Paulos ............... A61B 17/1764
606/96
5,928,232 A 7/1999 Howland et al.
(Continued)

FOREIGN PATENT DOCUMENTS

CN 206560458 U 10/2017
DE 4219939 12/1993
(Continued)

OTHER PUBLICATIONS

Berry et al., Personalised image-based templates for intra-operative guidance, Proceedings of the Institution of Mechanical Engineers, Part H: Journal of Engineering in Medicine, vol. 219, pp. 111-118, 2004.
(Continued)

*Primary Examiner* — Marcela I. Shirsat
(74) *Attorney, Agent, or Firm* — Meunier Carlin & Curfman LLC

(57) ABSTRACT

A cutting guide for periacetabular osteotomy comprises at least one first main body having a longitudinal opening for the insertion of a cutting instrument, extending from a first end to a second end of the first main body and at least two positioning and fixing arms extending away from the first main body from opposite sides with respect to the longitudinal opening, in order to correctly position the first main (Continued)

body on a bone and fix it thereto through respective fastening members.

15 Claims, 6 Drawing Sheets

(52) U.S. Cl.
CPC ....... *A61B 17/1739* (2013.01); *A61B 17/1742* (2013.01); *A61B 2017/568* (2013.01)
(58) Field of Classification Search
CPC ... A61B 17/152; A61B 17/17; A61B 17/1739; A61B 17/1742; A61B 17/56; A61B 2017/568
USPC ............................................ 606/87, 96, 104
See application file for complete search history.

(56) References Cited

U.S. PATENT DOCUMENTS

| | | | |
|---|---|---|---|
| 6,007,537 | A | 12/1999 | Burkinshaw et al. |
| 8,758,357 | B2 | 6/2014 | Frey |
| 8,870,889 | B2 | 10/2014 | Frey |
| 9,198,678 | B2 | 12/2015 | Frey et al. |
| 9,642,633 | B2 | 5/2017 | Frey et al. |
| 9,987,024 | B2 | 6/2018 | Frey et al. |
| 2002/0123668 | A1 | 9/2002 | Ritland |
| 2007/0066977 | A1 | 3/2007 | Assell et al. |
| 2008/0114370 | A1 | 5/2008 | Schoenfeld |
| 2011/0319745 | A1 | 12/2011 | Frey |
| 2012/0053590 | A1 | 3/2012 | Allen et al. |
| 2012/0130382 | A1 | 5/2012 | Iannotti et al. |
| 2012/0245587 | A1 | 9/2012 | Fang et al. |
| 2013/0053854 | A1 | 2/2013 | Schoenefeld et al. |
| 2013/0123850 | A1 | 5/2013 | Schoenfeld et al. |
| 2013/0218163 | A1 | 8/2013 | Frey |
| 2014/0074099 | A1* | 3/2014 | Vigneron ............... A61B 17/15 606/87 |
| 2014/0163565 | A1 | 6/2014 | Bollinger |
| 2014/0358152 | A1 | 12/2014 | Condino et al. |
| 2015/0320430 | A1 | 11/2015 | Kehres et al. |
| 2018/0042619 | A1 | 2/2018 | Frey et al. |
| 2018/0177512 | A1 | 6/2018 | Hogan et al. |
| 2021/0077119 | A1* | 3/2021 | Siccardi ............... A61B 17/151 |

FOREIGN PATENT DOCUMENTS

| | | |
|---|---|---|
| DE | 102016218965 | 4/2018 |
| EP | 2502582 | 9/2012 |
| EP | 2749235 | 7/2014 |
| JP | 2015208566 A | 11/2015 |
| JP | 2016524506 | 8/2016 |
| TW | 200908927 | 3/2009 |
| TW | 201 238 556 | 10/2012 |
| WO | 9600049 | 1/1996 |
| WO | 2012/156466 A1 | 11/2012 |
| WO | 2013158521 | 10/2013 |
| WO | 2014070889 | 5/2014 |
| WO | 2014090908 | 6/2014 |
| WO | 2014197844 | 12/2014 |
| WO | 2016075581 | 5/2016 |
| WO | 2016075660 | 5/2016 |
| WO | 2018055494 | 3/2018 |
| WO | 2018055518 | 3/2018 |

OTHER PUBLICATIONS

Brussel et al., Medical Image-Based Design of An Individualized Surgical Guide For Pedicle Screw Insertion, 18th Annual International Conference of the IEEE Engineering in Medicine and Biology Society, Amsterdam, pp. 225-226, 1996.
Lu et al., A novel computer-assisted drill guide template for placement of C2 laminar screws, Eur Spine J, vol. 18, pp. 1379-1385, 2009.
Lu et al., A Novel Patient-Specific Navigational Template for Cervical Pedicle Screw Placement. SPINE, vol. 34, No. 26, pp. E959-E964, 2009.
Lu et al., Rapid prototyping drill guide template for lumbar pedicle screw placement, Chinese Journal of Traumatology, vol. 12(3), pp. 171-177, 2009.
Popescu et al., Design and Rapid Manufacturing Of Patient-Specific Spinal Surgical Guides: A Survey, Proceedings in Manufacturing Systems, vol. 7, Issue 2, pp. 115-120, 2012.
Radermacher, Klaus, Computer Assisted Orthopaedic Surgery with Individual Templates, Helmholtz-Institute for Biomedical Engineering, 2 pages, 1997.
Ryken et al., Image-based drill templates for cervical pedicle screw placement, J Neurosurg Spine vol. 10, pp. 21-26, 2009.
English Translation of Notice of Reasons of Refusal in JP 2019-536354, dated Feb. 10, 2020, 7 pages.
International Search Report and Written Opinion issued for Application No. PCT/IB2017/055688, dated Nov. 16, 2017. 11 pages.
International Search Report and Written Opinion issued for Application No. PCT/IB2017/055588, dated Nov. 22, 2017. 13 pages.
English Translation of Notice of Reasons of Refusal in JP 2019-536348, dated Feb. 27, 2020, 14 pages.
International Search Report and Written Opinion issued for Application No. PCT/IB2019/053765 dated Aug. 6, 2019. 15 pages.
International Search Report and Written Opinion, issued by the International Searching Authority (ISA/EP) in Application No. PCT/IB2018/060161 dated Apr. 5, 2019. 9 pages.
International Search Report and Written Opinion for International Application No. PCT/IB2019/058162 dated Jan. 22, 2020. 16 pages.
Office Action issued for U.S. Appl. No. 16/333,057, dated Jul. 30, 2020.
Office Action issued for U.S. Appl. No. 16/333,055, dated Dec. 8, 2020.
International Search Report and Written Opinion, issued by the International Searching Authority (ISA/EP) in Application No. PCT/IB2019/060161 dated Apr. 2, 2020. 11 pages.
International Search Report and Written Opinion, issued by the International Searching Authority (ISA/EP) in Application No. PCT/IB2018/060160 dated Apr. 5, 2019. 13 pages.
Office Action for U.S. Appl. No. 16/956,250, dated May 2, 2022. (32 pages).

* cited by examiner

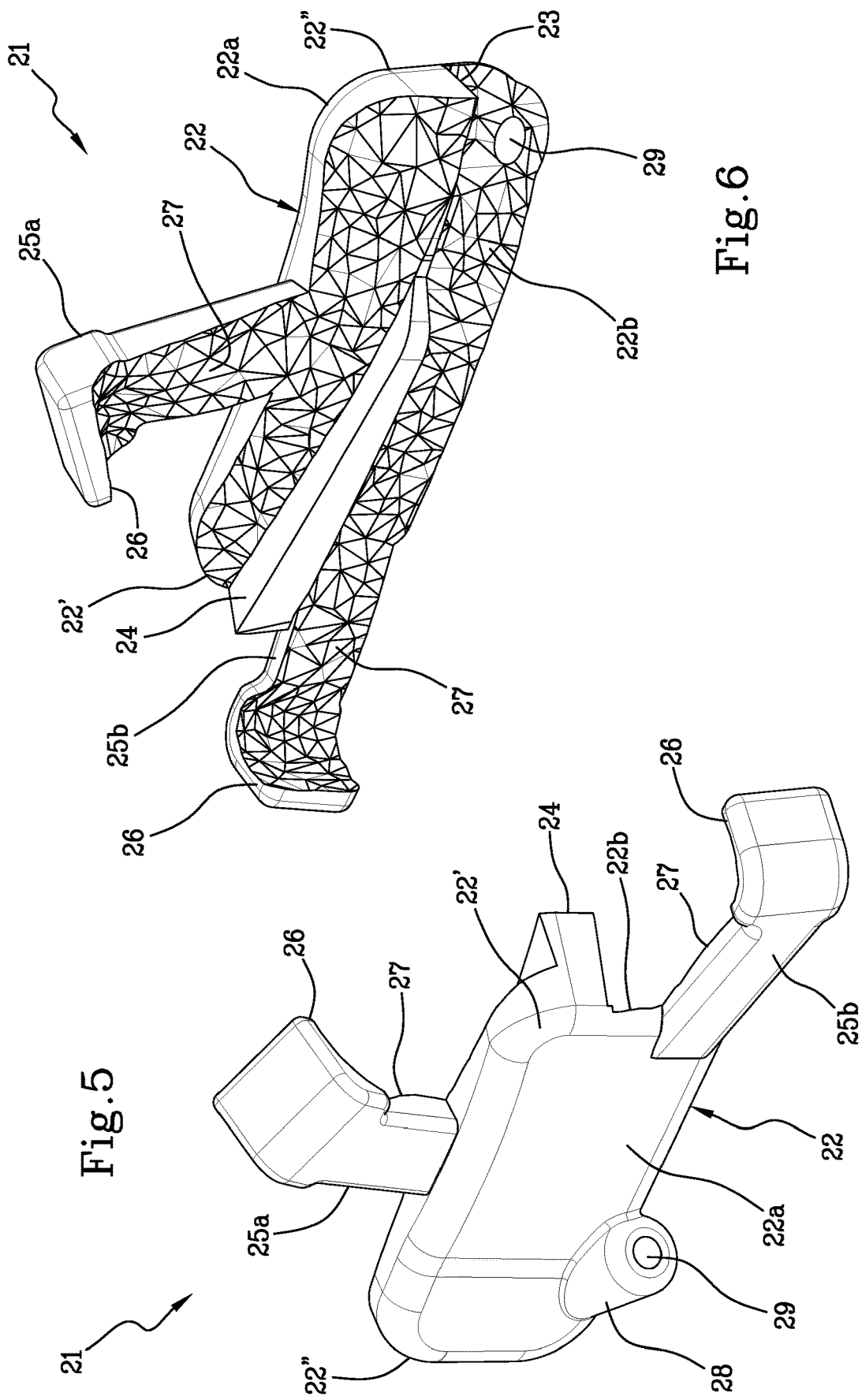

CUTTING GUIDE FOR PERIACETABULAR OSTEOTOMY AND KIT FOR PERIACETABULAR OSTEOTOMY

The present invention relates to a cutting guide for periacetabular osteotomy.

Periacetabular osteotomy is a surgical procedure that has to be performed to treat hip dysplasia, a condition in which the hip joint develops abnormally so that the head of the femur gradually becomes dislodged from the acetabulum.

The hip joint is formed by the acetabulum and the head of the femur. When hip dysplasia occurs, the head of the femur does not fit firmly in the acetabulum and easily becomes dislocated. Thus, the two parts (concave and convex) of the joint do not fit together perfectly and this can result in a state of general instability of the articular system, making the hip very susceptible to dislocation.

Periacetabular osteotomy, or PAO, is a highly specialised procedure that has evolved over many years, the aim of which is to realign the acetabulum in order to restore the physiological morphology of the joint.

The objective of surgical treatment of dysplasia is to restore congruency of the joint and thus normal biomechanical forces: periacetabular osteotomy is performed to increase the area of contact, reduce instability-related stress and normalise load forces.

Periacetabular osteotomy involves cutting the bone around the acetabulum and detaching it completely from the hip bone, without interrupting the continuity of the bone between the upper part and the lower part of said hip bone. In other words, it consists in creating a fracture in the bone between the hip bone and the acetabulum in order to separate the bone into two parts. The acetabulum fragment is then translated and redirected so that the acetabulum is in the correct position, and then fixed to the pelvis using screws and metal wire.

When performed by experienced surgeons, this highly specialised surgical procedure produces excellent clinical, radiographic and functional results, by realigning the two parts of the bone in a new and mechanically correct position.

This method currently involves a number of osteotomies around the joint, in order to completely free the acetabulum so that it can be redirected and fixed in the best position.

However, all cutting is done freehand by the surgeon, following a line determined in advance in the preoperative stage.

This method of cutting clearly involves difficulties and carries some risks for the patient, as the success of the operation depends entirely on the experience and skill of the surgeon.

Owing to the vibrations caused by the bone cutting instrument, there is always a risk of not following the cut properly or of touching soft tissue.

Once the osteotomies are complete, the acetabular fragment is completely mobile and is redirected in order to gain the required coverage of the femur head and angle of version under intraoperative image intensifier control.

Therefore, the two parts into which the bone has been cut are also rotated and realigned by sight, and the surgeon rotates the acetabulum until gaining the correct alignment by examining antero-posterior projections of the entire pelvis during the surgical procedure.

There is certainly also a high risk of human error during the realignment step.

The purpose of the present invention is therefore to provide a cutting guide for periacetabular osteotomy that assists the surgeon during the cutting step, reducing the risks for the patient due to human error to a minimum and shortening operating times.

A further purpose of the present invention is to provide a cutting guide for periacetabular osteotomy that defines and clearly indicates the cutting line to the surgeon in order to achieve an accurate cut without the risk of touching soft tissue or deviating from the predefined cutting line.

Yet another purpose of the present invention is to propose a kit for performing periacetabular osteotomy that not only makes it possible to achieve an accurate cut but also a correct realignment of the two parts into which the bone has been cut according to the physiological morphology of the joint.

These and further characteristics, and the respective advantages, of a cutting guide for periacetabular osteotomy and a kit for periacetabular osteotomy will be more apparent from the description that follows of a preferred and non-exclusive embodiment represented solely by way of non-limiting example in the accompanying figures, in which:

FIG. 5 is a perspective view from above of an aligner included in a kit for periacetabular osteotomy;

FIG. 6 is a perspective view from below of the aligner shown in FIG. 5;

Figure 1:
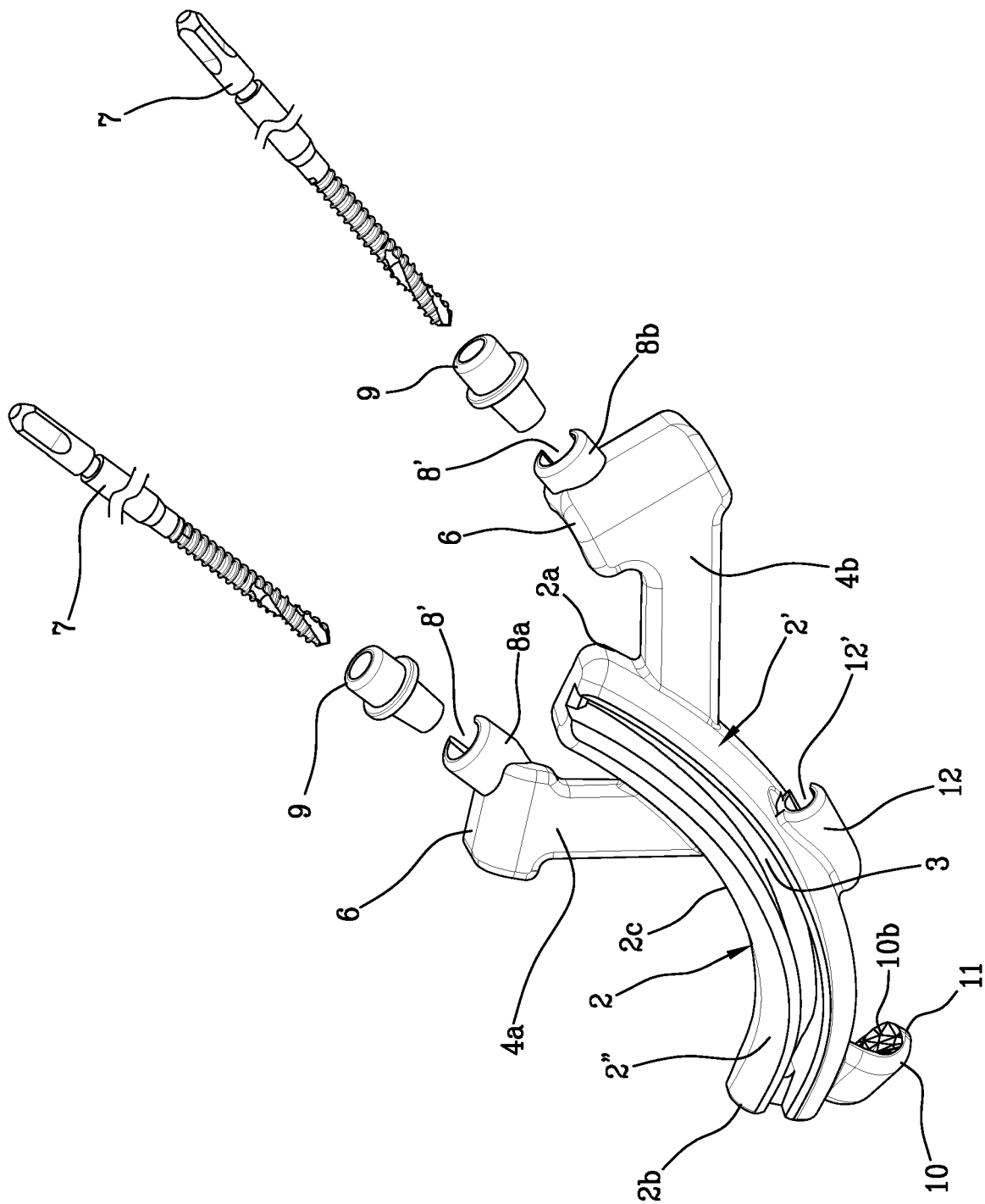
FIG. 1 is a perspective view from above of a first main body of a cutting guide for periacetabular osteotomy according to the present invention.

In the accompanying figures, reference numeral 1 globally denotes a cutting guide for periacetabular osteotomy, according to the present invention.

Figure 7:
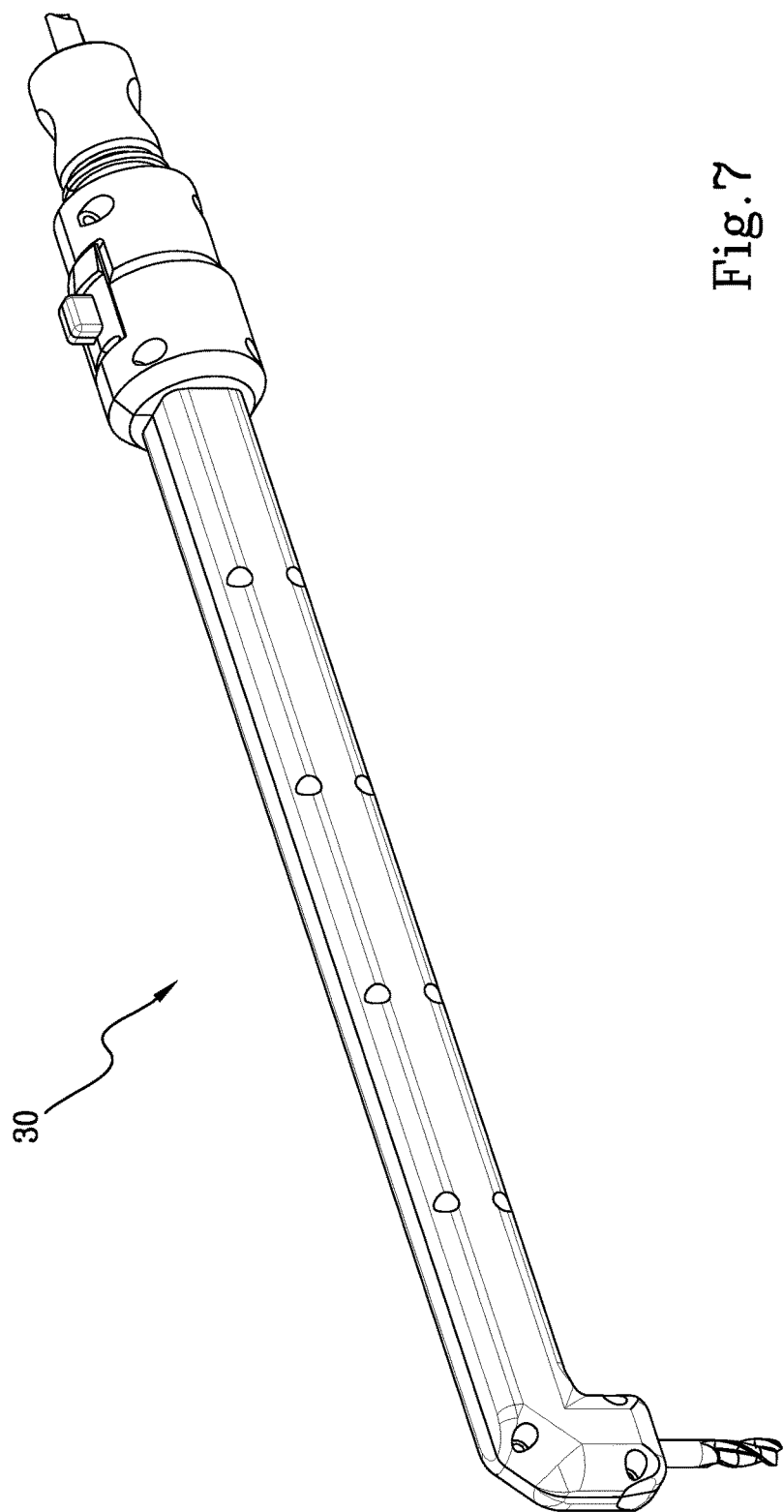
FIG. 7 illustrates a bone cutting instrument.

The cutting guide 1 is a device used to assist the surgeon during an operating step, in particular during the cutting of the bone B, by defining a univocal cutting path to be followed by the bone cutting instrument 30 (FIG. 7).

The cutting guide 1 comprises at least one first main body 2 (FIGS. 1 and 2) having a longitudinal opening 3 for the insertion of a cutting instrument 30. This first main body 2 may also be referred to as the proximal guide.

Said longitudinal opening 3 essentially extends from a first end 2a to a second end 2b of the first main body 2 along the longitudinal axis of extension of the first main body 2.

Said opening 3 is such that when the proximal guide 2 is coupled to the bone, the underlying bone is visible through it.

The first main body 2 has a first portion 2' that extends from the first end 2a to an intermediate section 2c, and a second portion 2" that extends from the intermediate section 2c to the second end 2b.

The cut to be performed along the bone is not rectilinear but must follow a periacetabular osteotomy path: for that reason the first main body 2, which comprises the longitudinal opening 3 that follows the cutting line, is not rectilinear, but has a curvilinear shape. Likewise, the opening 3 follows the exact curvilinear shape of the periacetabular osteotomy path.

The first main body 2 comprises, in correspondence with the first portion 2', at least two positioning and fixing arms 4*a* and 4*b*, extending away from the first main body 2. Each arm 4*a* and 4*b* extends away from the first main body 2 towards the first end 2*a*, from opposite sides with respect to the longitudinal opening 3.

The purpose of said arms 4*a* and 4*b* is to correctly position the cutting guide 1, in particular the first main body 2 of the guide 1, on the bone B to be cut.

Both the first main body 2 and the positioning and fixing arms 4*a*, 4*b* have a lower surface 5, i.e., the surface that is coupled to the patient's bone, shaped on the anatomy of the patient's bone to enable the correct and univocal positioning thereof. In other words, the lower surface 5 is the negative of the surface of the bone to which the first main body 2 must be coupled.

In addition, the positioning and fixing arms 4*a*, 4*b* have at least one fastener lip 6 suitable to grasp an edge of the bone to be cut and having lower edges shaped so that, like the lower surface 5, they are shaped on the anatomy of the patient.

Each positioning and fixing arm 4*a*, 4*b* is coupled to a respective fastening member 7 for fixing it to the bone to be cut.

Figure 3:
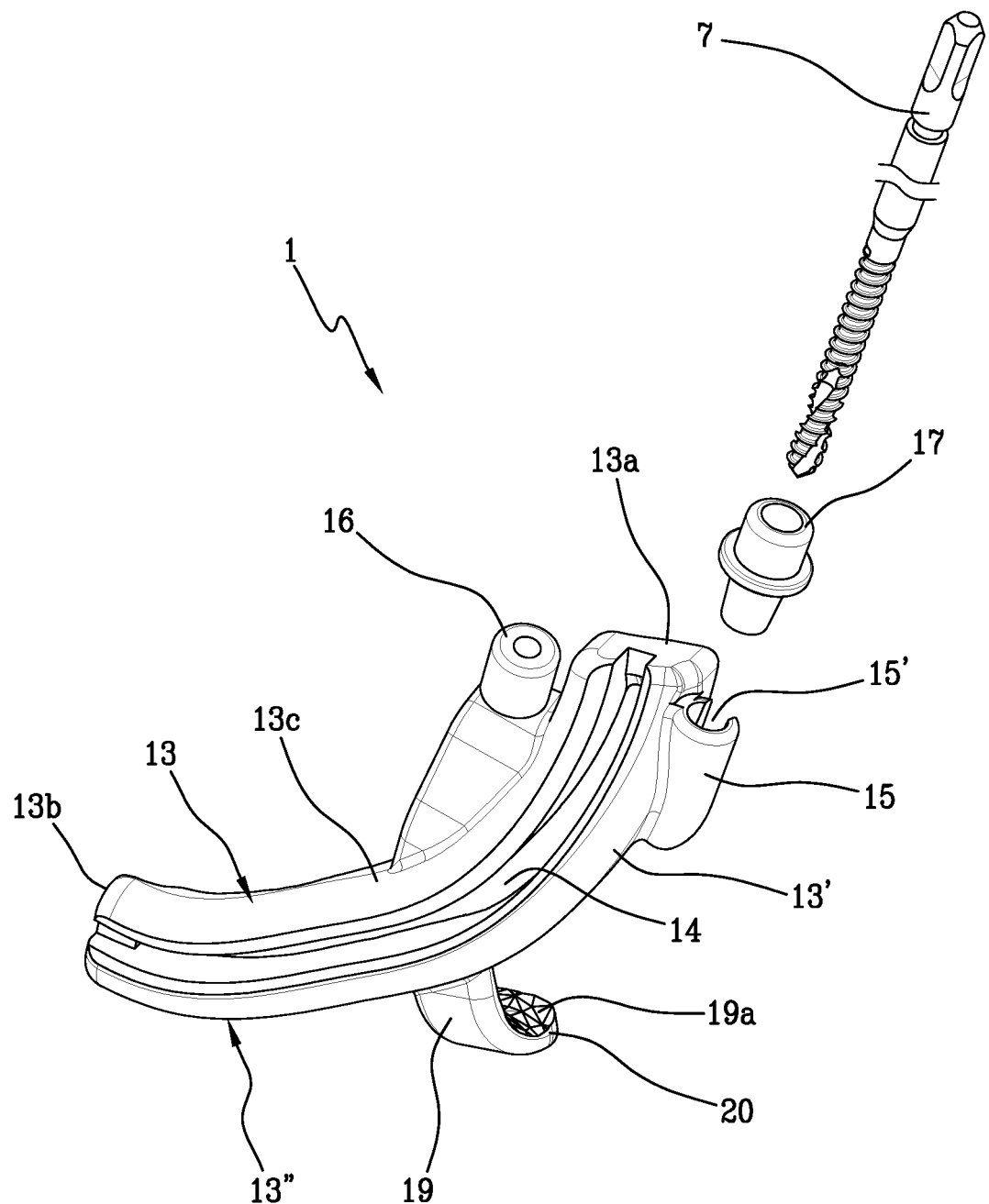
FIG. 3 is a perspective view from above of a second main body of a cutting guide for periacetabular osteotomy according to the present invention.

A typical fastening member is, for example, a surgical screw, a pin, or a cortical screw (Schanz screw), as can be seen in FIGS. 1, 3 and 9.

The fastening members 7 to which the first main body 2 is coupled are only illustrated in some of the images.

Specifically, each positioning and fixing arm 4*a*, 4*b* comprises a respective sleeve, a first sleeve 8*a* and a second sleeve 8*b*, into which a respective fastening member 7 can be inserted.

Figure 2:
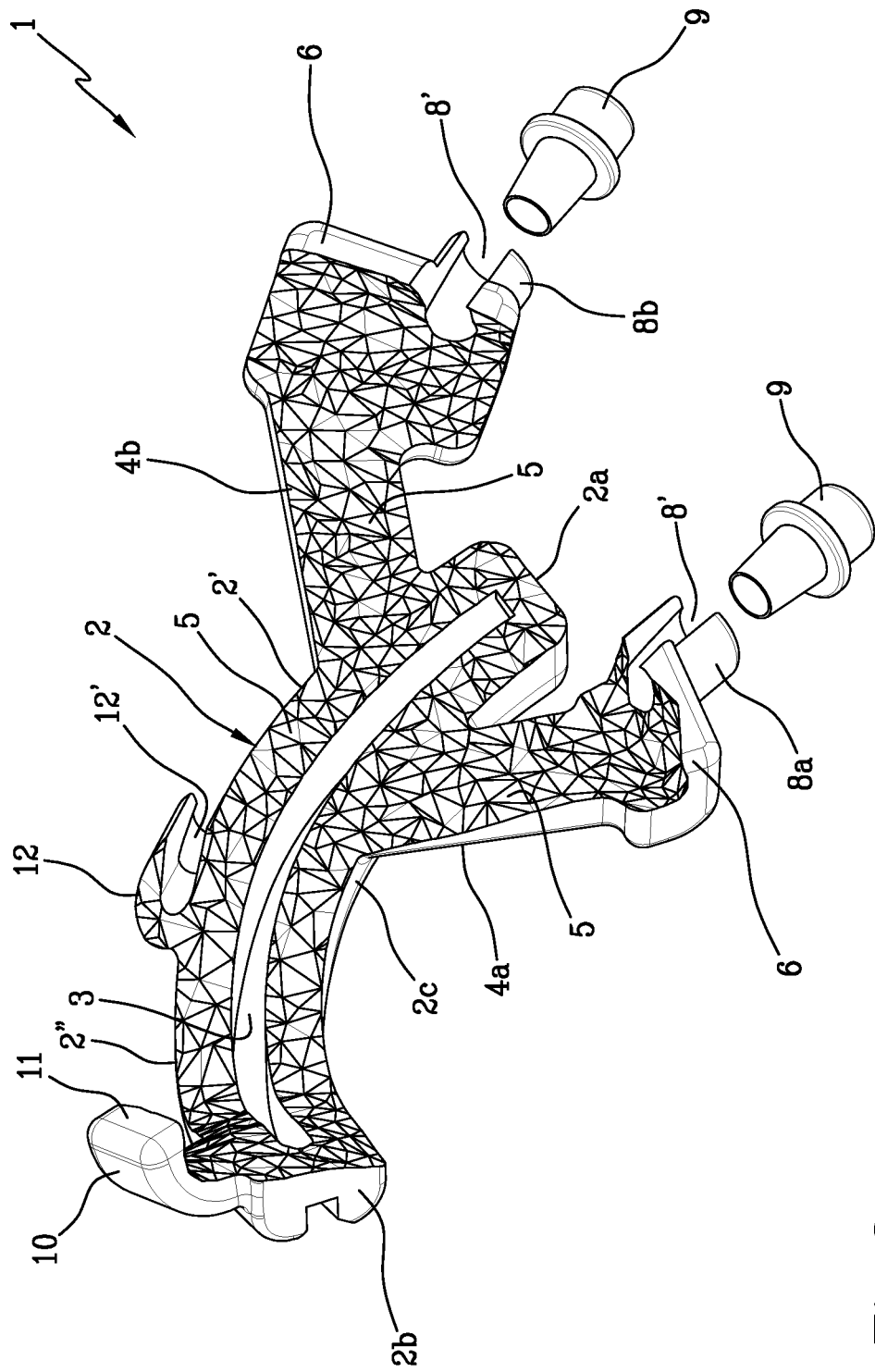
FIG. 2 is a perspective view from below of the first main body of a cutting guide for periacetabular osteotomy illustrated in FIG. 1.

As shown in FIGS. 1 and 2, the sleeves 8*a*, 8*b* protrude from the respective arms 4*a*, 4*b* with a collar.

To achieve a stable connection between the first main body 2 and the fastening members 7, there may be bushings 9 that can be fitted over each sleeve 8*a*, 8*b* in correspondence with the respective collars.

This additional connection serves to achieve a more secure fastening of the structure, and thus of the proximal guide or first main body 2 to the fastening member 7 so as to limit the vibrations transmitted by the cutting instrument to the entire device with the subsequent risk of misalignment of the guide.

The first sleeve 8*a* and the second sleeve 8*b* may each have a side opening 8' to allow the easy disengagement of the first main body 2 from the fastening members 7 if the latter have to be left in place or have to be extracted after the proximal guide or first main body 2 has been removed. In that configuration, the first sleeve 8*a* and the second sleeve 8*b* of the first main body 2 have a substantially C-shaped cross section.

Alternatively, the first sleeve 8*a* and the second sleeve 8*b* are closed at the side, and have a circular cross section.

The first main body 2 further comprises a positioning pin 10 projecting from and arranged in proximity to the second end 2*b* of the first main body 2.

The purpose of said pin 10, like the arms 4*a* and 4*b*, is to correctly position the first main body 2 on the bone to be cut and make it possible to grip the bone firmly. To provide a stable and univocal connection, the pin 10 has a lower surface 10*b*, the one that abuts against the bone, shaped on the anatomy of the patient's bone; furthermore, the pin also comprises at least one fastener lip 11, which is also shaped on the anatomy of the patient, that grasps an edge of the bone to be cut.

Along its longitudinal extension, essentially in correspondence with the intermediate section 2*c*, the first main body 2 has a third sleeve 12 (visible in FIGS. 1 and 2) adapted for the insertion of a respective third fastening member 7, so as to achieve a third point for connecting the first main body 2 to the bone to be cut.

As can be seen in FIGS. 1 and 2, the third sleeve 12 also has a side opening 12' to allow the disengagement of the first main body 2 from the respective fastening member 7 inserted in the third sleeve 12. In order to more clearly define the fastening member 7 coupled to the third sleeve 12, this fastening member will also be referred to hereinafter as the third fastening member 7 or as the fastening and reference member. As described more fully below, this third fastening member 7 is used as a reference member for the correct positioning of the first main body 2 and of two other elements that are part of the present invention, and specifically a second main body 13 of the cutting guide 1 and a further main body 22 of an aligner 21. These elements will be described in detail later on in this document.

Going back to the first main body 2, in this case, the fastening member 7 inserted in the third sleeve 12 remains in place in the bone even after the first main body 2 has been removed. It must therefore be possible to separate the latter from the fastening screw easily and without causing any misalignment of the screw or of the partially cut bone.

Specifically, said third fastening member 7 remains in place until the end of the operation as it serves as a further point of reference for the correct positioning of additional elements, as will be explained later on.

The cutting guide 1 according to the present invention further comprises a second main body 13 (FIGS. 3 and 4), which also has a longitudinal opening 14 for the insertion of the same cutting instrument 30 previously used with the first main body 2.

This second main body 13 may also be referred to as the distal guide.

The second main body 13 also has a first portion 13' that extends from a first end 13*a* to an intermediate section 13*c* of the second main body 13, and a second portion 13" that extends from this intermediate section 13*c* to a second end 13*b* of the second main body 13.

The longitudinal opening 14 of the second main body 13 extends from the first end 13*a* to the second end 13*b* of the second main body 13.

The second main body 13 also has a curvilinear shape to follow the path of the cut to be made along the bone, and thus to follow the periacetabular osteotomy path.

Therefore, the longitudinal opening 14 of the second main body 13 is not rectilinear either, but has a curvilinear shape to follow the exact periacetabular osteotomy path.

Figure 4:
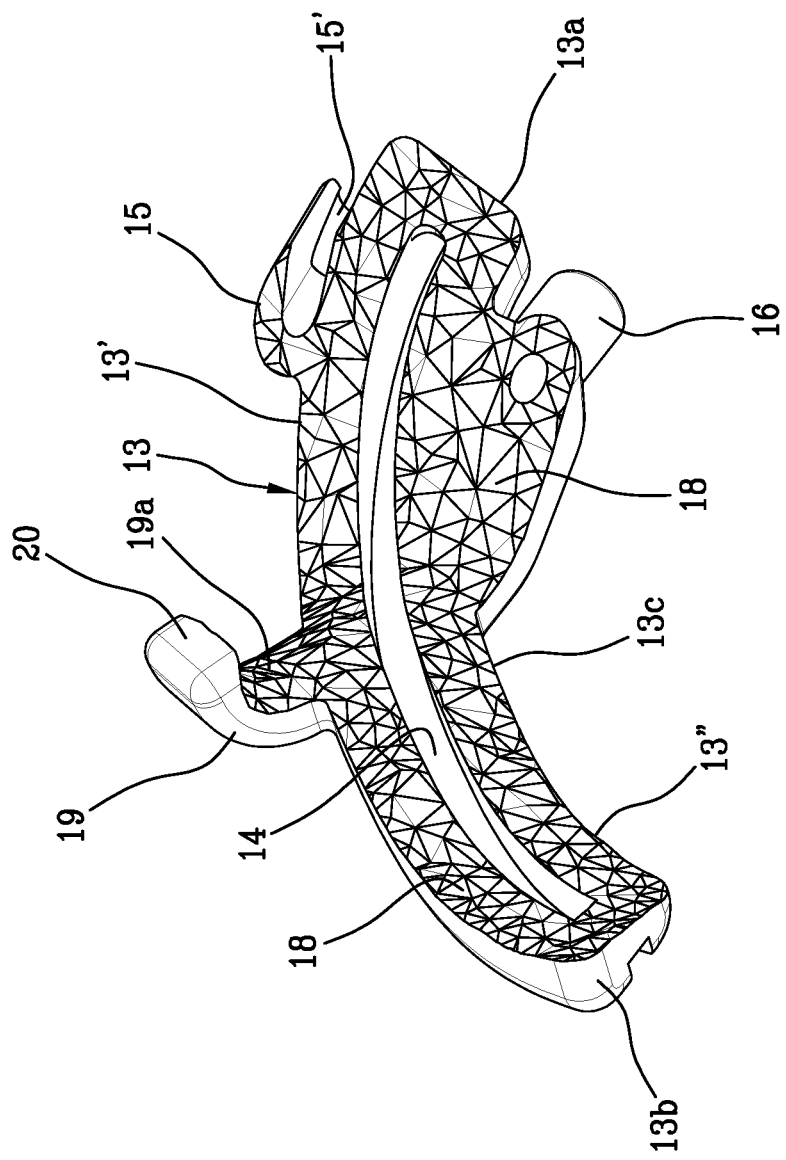
FIG. 4 is a perspective view from below of the second main body of a cutting guide for periacetabular osteotomy illustrated in FIG. 3.

As can be seen in FIGS. 3 and 4, the second main body 13 has a first portion 13' that is superimposable on the second portion 2" of the first main body 2.

The partial superimposition of the two guides, namely of the proximal and distal guides, is due to the sequence in which the two guides are used during the surgical procedure: the first part of the cut is performed using the first main body 2 (proximal guide) as the guide, and thus as the template for the cutting instrument, whereas the second part of the cut is performed using the second main body 13 (distal guide) as the cutting template. When the proximal guide used to make the first part of the cut has been removed and the distal guide has been fitted, there is a partial superimposition of the first portion 13' of the second main body 13 and the second portion 2" of the first main body 2, in order to ensure that the surgeon continues to make the cut correctly. In other words there is a partial superimposition of the longitudinal opening 14 of the second main body 13 and the cut that has already been made, in particular of the first part of the longitudinal opening 14 of the second main body 13 and the final part of the cut that has already been made and created in correspondence with the second portion 2" of the first main body 2. Following on from this partial superimposition, the longitudinal opening 14 of the second main body 13 continues the exact cutting line along the periacetabular osteotomy path, to complete the cutting of the entire bone. The second main body 13 has a first sleeve 15, adapted for the insertion of a respective fastening member 7, arranged in proximity to the first end 13a of the second main body 13.

The first sleeve 15 of the second main body 13 has a side opening 15' to allow the disengagement of the second main body 13 from the respective fastening member 7 (or third fastening member) inserted in the first sleeve 15.

This opening permits the fast and secure connection of the second main body 13 to the fastening member 7 already in place in the bone.

In actual fact, the first sleeve 15 of the second main body 13 is coupled to the fastening member 7 that was previously inserted in the third sleeve 12 of the first main body 2. As mentioned above, this is because the first portion 13' of the second main body 13 is superimposable on the second portion 2" of the first main body 2.

Furthermore, the second main body 13 has a second sleeve 16, suitable for the insertion of a respective fastening member 7, arranged in proximity to the first end 13a of the second main body 13.

This second sleeve 16 is closed, and so, unlike the sleeves described previously, does not have a side opening.

To achieve a stable connection between the second main body 13 and the respective fastening member 7 inserted in the first sleeve 15, a bushing 17 is fitted over the sleeve 15.

As mentioned above, while the fastening member 7 that can be coupled to the first sleeve 15 of the second main body 13 is the same fastening member 7 that was previously coupled to the third sleeve 12 of the first main body 2, the fastening member 7 inserted in the second sleeve 16 of the second main body 13 is a cortical screw exclusively dedicated to the second main body 13.

In order for the second main body 13 to be stably and univocally coupled to the bone to be cut, the lower surface 18 of the second main body 13, that is to say, the surface that faces and is coupled to the bone, is shaped on the anatomy of the patient's bone and thus follows the negative of the surface of the bone.

For greater stability and a more correct positioning of the second main body 13 on the bone to be cut, there is also a positioning pin 19 that extends from the second main body 13 in correspondence with the intermediate section 13c of the second main body 13.

The positioning pin 19 further comprises a fastener lip 20 to grasp an edge of the bone to be cut, and has a lower surface 19a that is coupled directly to the bone, shaped on the anatomy of the patient's bone, to permit the correct positioning of the second main body 13.

The present invention also relates to a kit for periacetabular osteotomy comprising a cutting guide 1 according to that described above, at least one fastening member 7, for example a surgical screw, pin or cortical screw (Schanz screw), that can be coupled to the cutting guide, at least in a first operating step, and an aligner 21 that can be coupled at least to the fastening member 7 (or third fastening member) that can be inserted in the sleeve shared by the first main body 2 and the second main body 13, in at least a second operating step.

Said aligner 21 (FIGS. 5 and 6) comprises a main body 22 with an upper surface 22a and a lower surface 22b that is coupled to the patient's bone. Said lower surface 22b is shaped on the final and correctly aligned anatomy of the patient's bone and follows the negative of the surface of the bone as it must be in the correctly aligned configuration.

The lower surface 22b, which can be seen in FIG. 6, is not planar but has at least one difference in height created by a shoulder or step 23 (FIG. 6) and/or by a ridge or rib 24 (FIGS. 5 and 6) defining abutment surfaces against which the two portions into which the bone is cut abut to assume the correct mutual alignment.

The shape of the aligner 21, in particular the shape of the lower surface 22b, is defined and established in the preoperative planning stage.

The main body 22 of the aligner 21 further comprises at least two positioning and fixing arms 25a and 25b. Each arm 25a and 25b extends away from the main body 22 of the aligner 21, towards a first end 22'.

The purpose of said arms 25a and 25b is to correctly position the aligner 21 on the cut bone. In detail, the arm 25b is positioned on the fixed bone segment, while the arm 25a is positioned on the bone segment that is moved only when this has been repositioned after being manually realigned by bringing the bone segment that is moved up against the abutment surfaces 23 and 24 on the lower surface 22b of the aligner 21. The positioning and fixing arms 25a, 25b have at least one fastener lip 26 suitable to grasp an edge of a respective part into which the bone has been cut and each has a respective lower surface 27 shaped so that, like the lower surface 23, it is shaped on the anatomy of the patient.

The aligner 21 has, in proximity to a second end 22" of the main body 22, a sleeve 28 provided with a through axial hole 29 suitable for the insertion of a respective fastening member 7 (third fastening member) to be fixed to the bone to be cut. In particular, the same fastening member 7 that was coupled, in the first operating step, to the third sleeve 12 of the first main body 2 and then to the first sleeve 15 of the second main body 13, is inserted in this sleeve 28.

Said third fastening member 7 defines the point of reference for the correct positioning of the two main bodies 2 and 13 of the cutting guide 1 in the first operating step when the bone is cut, and for the aligner 21 in the second operating step in which the bone is repositioned and realigned.

After cutting the bone, the shape of the lower surface 22b of the aligner 21, in particular the differences in height and the inclinations given by the shoulder 23 and/or by the ridge 24, forces the two parts into which the bone has been cut to arrange themselves in relation to one another in accordance with the correct anatomical alignment defined in the preoperative planning stage.

The two parts of bone are rotated and translated manually by the surgeon, following the new configuration as suggested and determined by the shape of the lower surface 22b of the main body 22 of the aligner 21.

When the two parts into which the bone has been cut have been arranged in the correct position in relation to each other, they are fixed in that position using specific positioning and fixing screws.

During the operating step, the first main body 2 is positioned on the bone to be cut in a univocal and predetermined position, not only by means of the lower surface 5 but also the positioning and fixing arms 4a, 4b, each provided with the fastener lip 6.

Once the first main body 2 has been positioned, the fastening members 7 are inserted in the sleeves 8a, 8b of the arms 4a and 4b. The first main body 2 is then stably fixed to the fastening members 7 by means of the bushings 9.

Alternatively, if the main body has sleeves that are closed at the side, it may not be necessary to fit said bushings 9.

The first main body 2 is fixed to the bone by means of a third fastening member 7 inserted in the third sleeve 12 arranged in correspondence with the intermediate section 2c of the second main body 2.

With the first main body 2 thus secured to the bone to be cut, the actual cut can be made using a bone cutting instrument 30.

The latter is generally a bone cutter, better illustrated in FIG. 7, that is inserted into the opening 3 of the first main body 2.

The bone cutter is thus guided by said opening 3 to cut the bone along the exact periacetabular osteotomy path defined in the preoperative stage.

The cutting instrument 30 thus follows the entire opening, from the first end 2a to the second end 2b of the first main body 2. The first part of the bone is thus cut.

When the first cut has been completed, the cutter 30 is moved away from the patient's body, and the bushings 9 are removed to allow the disengagement of the first main body 2 from the fastening members 7, which are then also removed.

The third fastening member 7 inserted in the third sleeve 12 must instead remain in place, until the end of the operation, including the bone realignment step: in other words, the fastening member 7 inserted in the third sleeve 12 must also remain in the bone during the second part of the cut which is performed with the second main body 13 or distal guide coupled to the bone and also during the alignment step since, as stated previously, it is the point of reference for the three main bodies: the first main body 2 and the second main body 13 of the cutting guide 1 and the main body 22 of the aligner 21.

The angle at which the fastening members 7 are inserted into the bone is established by the inclination of the sleeves 8a and 8b with respect to the first main body 2.

Said inclination is determined by the need to fix said fastening members 7 stably to the bone structure, without damaging the latter and so as to create the largest possible area of interaction between the bone and the fastening members; for these reasons it is defined in the preoperative planning stage, on the basis of the bone anatomy.

The main body 2 is removed from the position in which it is coupled to the bone through the side openings 8' obtained along the sleeves 8a and 8b and the opening 12' along the third sleeve 12.

If the sleeves 8a and 8b do not have the side openings 8', the fastening elements 7 can be removed first in order to remove the main body 2.

The first main body 2 is thus used to make the first part of the cut, which must be completed using the second main body 13. After removing the first main body 2, the second main body 13 must be positioned.

In particular, to ensure the correct alignment of the distal guide and be able to continue cutting in the right direction, said guide has a first portion 13' that is superimposable on the second portion 2" of the proximal guide 2.

In actual fact, the fastening member 7 that was previously inserted in the third sleeve 12 and is still fixed to the bone is used to connect it to the first sleeve 15 of the second main body 13.

The positioning pin 19 of the distal guide 13 is arranged exactly where the positioning pin 10 of the proximal guide 2 was attached.

When the second main body 13 is in place, a new fastening member 7, the fourth, is inserted in the second sleeve 16, using the third fastening member 7 and the positioning pin 19 as references.

A connecting bushing 17 is connected to the second sleeve 16 to connect the fastening member securely to the second main body 13, in order to prevent the vibrations transmitted by the cutter from causing any movement of said distal guide.

The actual cut is then made, by inserting the bone cutting instrument 30 into the longitudinal opening 14, from the first end 13a to the second end 13b.

Once the second part of the cut is also complete, the second main body 13 is removed by separating the bushing 17 from the second sleeve 16 and then extracting the fastening member 7 from inside the second sleeve 16.

The second main body 13 can thus be removed from the surgical site. The fastening member 7 coupled to the first sleeve 15 must, instead, remain in place, fixed to the bone. The next step of the surgical procedure consists in realigning the two parts B', B" into which the bone has been cut so that they assume the correct anatomical position, as described later on.

Only the fastening member 7 (third fastening member) that was used to anchor both the first main body 2, in correspondence with the third sleeve 12, and the second main body 13, in correspondence with the first sleeve 15, remains fixed in the bone.

For the second operating step, in which the bone is realigned, the aligner 21 must be connected to this latter fastening member 7.

The aligner 21, in particular the sleeve 28, is fitted over this fastening member 7 from the top.

The geometry of the lower surface 22b of the aligner 21 is defined in advance in the preoperative planning stage and defines the mutual position that the two parts into which the bone has been cut must assume when correctly aligned. In other words, once the aligner 21 has been coupled to the two parts into which the bone has been cut via the third fastening member 7 and the arms 25a and 25b, each coupled, respectively, to one of the two parts into which the bone has been cut, it will force the two parts into which the bone has been cut to assume the correct mutual alignment thanks to the differences in height on the lower surface 22b which define abutment surfaces against which said two portions into which the bone has been cut abut.

As mentioned above, the lower surface 22b of the aligner 21 may have a shoulder or step 23, a ridge or rib 24, or both.

In order for the two parts into which the bone has been cut to be able to rotate and translate correctly to assume the correct final anatomical alignment, after physically separating the bone into two parts, breaking the two end edges if these have not been cut by the cutter, the surgeon moves the two parts of the bone manually, matching them with the lower surface 22b of the aligner 21, so that one or the other part of the bone abuts against the ridge 24 or the shoulder 23.

When the two portions of the bone are aligned and the final relative position of the two parts has been defined, connecting screws are inserted between the two parts into which the bone has been cut to block them and stabilise their position and relative rotation.

Lastly, the third fastening member 7 and the aligner 21 are removed.

The invention brings notable advantages with respect to the current operating technique that, as mentioned above, does not envisage the use of a cutting guide, but cutting the bone freehand using bone cutters.

The present invention, on the other hand, proposes a cutting guide in order to perform cutting accurately and safely, which is of considerable help to the surgeon during the operating step in that it defines a previously established cutting path.

Moreover, a significant advantage of the present invention is the control achieved over the final realignment, as compared to the methods that are currently known, when this is only done by hand or under fluoroscopic control.

The cutting guide, as presented in the present description, actually envisages two cutting guides that are used in sequence. However, it can envisage a single cutting guide defining the entire path of the cut to be made.

The surgeon simply has to position the guide, the lower surface of which is the negative of the bone to which it must be coupled, and fix it to the bone using appropriate fastening members.

Once the guide has been stably connected to the bone, the surgeon only has to insert the bone cutting instrument, for example the cutter, into the channel or central opening obtained longitudinally along the guide. This opening follows the cutting path defined in the preoperative stage: the cutter is made to slide and move along said opening to cut the bone accurately and safely without any risk for the patient.

After making the cut, the aligner is used to move the two portions of bone and force them to assume the correct alignment. The surgeon is again assisted in this second operating step and has an instrument that enables him or her to achieve the most correct alignment, without merely having to rely on a visual evaluation made on the spot, which could also be difficult owing to the presence of blood or soft tissue obstructing the view of the surgical site.

When the kit for periacetabular osteotomy is used, the risk of error is reduced to a minimum, the cut is easier for the surgeon to perform and the acetabulum is more accurately realigned in accordance with the preoperative plan, operating times are significantly shortened, the operation is less invasive for the patient and the overall success rate for the operation improves.

The invention claimed is:

1. A cutting guide for periacetabular osteotomy comprising:
   at least a first main body having a longitudinal opening defining a cutting line for the insertion of a cutting instrument, extending from a first end to a second end of said first main body, said first main body has a first portion extending from said first end to an intermediate section and a second portion extending from said intermediate section to said second end, and
at least two positioning and fixing arms extending away from said first main body from opposite sides with respect to said longitudinal opening, the positioning and fixing arms being adapted to correctly position said first main body on a bone and fix it thereto through respective fastening members; and
   a second main body having a longitudinal opening defining a cutting line for the insertion of a cutting instrument, extending from a first end to a second end of said second main body, wherein said second main body has a first portion extending from a first end to an intermediate section of said second main body, and a second portion extending from said intermediate section to said second end of said second main body, wherein the second main body is formed separately from the first main body, wherein said first portion of said second main body has the same shape of and is superimposable on the second portion of said first main body such that, when replacing the first main body with the second main body, the cutting line defined by the longitudinal opening of the second main body continues the cutting line defined by the longitudinal opening of the first main body.

2. The cutting guide according to claim 1, wherein each of said positioning and fixing arms has a lower surface adapted to match a surface of a patient's bone to allow correct and univocal positioning, and at least one fastener lip adapted to grasp an edge of the bone to be cut; said positioning and fixing arms extending towards said first end of said first main body.

3. The cutting guide according to claim 1, wherein said positioning and fixing arms have a respective first sleeve and a second sleeve inside which a respective fastening member can be inserted, wherein each of said first and said second sleeves has a side opening to allow disengagement of the first main body from the fastening members.

4. The cutting guide according to claim 3, comprising a bushing that can be connected to a respective sleeve to achieve a stable connection between said first main body and said fastening members.

5. The cutting guide according to claim 1, comprising a positioning foot, projecting from said first main body, the positioning foot adapted to correctly position said first main body on a bone to be cut, wherein said positioning foot has a lower surface adapted to match a surface of a patient's bone to allow correct and univocal positioning, and at least one fastener lip adapted to grasp an edge of the bone to be cut; said positioning foot being located in the proximity of said second end of said first main body.

6. The cutting guide according to claim 3, comprising a third sleeve, connected to the first main body along its longitudinal extension, the third sleeve adapted for the insertion of a respective fastening member, the respective fastening member being adapted to provide a third point for connecting said first main body to the bone to be cut; wherein said third sleeve has a side opening to allow disengagement of said first main body from the respective fastening member inserted in said third sleeve.

7. The cutting guide according to claim 1, wherein said first main body has a curvilinear shape.

8. The cutting guide according to claim 1, wherein said second main body has a curvilinear shape.

9. The cutting guide according to claim 1, wherein said second main body has a first sleeve, adapted for the insertion of a respective fastening member, positioned in the proximity of the first end of said second main body, wherein said first sleeve of said second main body has a side opening to allow disengagement of the second main body from the respective fastening member inserted in said first sleeve.

10. The cutting guide according to claim 9, wherein said second main body has a second sleeve, adapted for the insertion of a respective fastening member, positioned in the proximity of the first end of said second main body.

11. The cutting guide according to claim 10, wherein said first sleeve of said second main body is connected to a bushing to provide a stable connection between said second main body and the respective fastening member.

12. The cutting guide according to claim 1, comprising:
   a positioning foot extending from said second main body, the positioning foot adapted to correctly position said second main body on said bone to be cut; said positioning foot being located in the proximity of the intermediate section of said second main body, wherein said positioning foot has a lower surface adapted to match a surface of the patient's bone to allow correct and univocal positioning, and at least one fastener lip adapted to grasp an edge of the bone to be cut.

13. A kit for periacetabular osteotomy comprising a cutting guide according to claim 1, at least one fastening member, which can be inserted in said cutting guide in a first operating step and is adapted to fix said first main body on a bone, and an aligner, which can be coupled to at least said one fastening member in a second operating step,
  wherein said aligner has a main body having an upper surface and a lower surface, the surfaces being adapted to couple with two bone parts that are to be aligned with each other, said lower surface being adapted to match a final anatomy when the two bone portions are correctly and mutually aligned,
  wherein said lower surface has at least one difference in height created by a shoulder or step and/or by a ridge or rib, which define abutment surfaces adapted to abut the bone to be cut to ensure correct mutual alignment of the two bone portions.

14. The kit according to claim 13, wherein said main body of the aligner comprises at least two positioning and fixing arms; each arm extending away from the main body of the aligner towards a first end, the arms being adapted to grasp an edge of a respective part into which the bone has been cut.

15. The kit according to claim 13, wherein said main body of said aligner has a sleeve provided with a through axial hole adapted for the insertion of a respective fastening member, the fastening member being adapted to be fixed to the bone to be cut.

* * * * *